United States Patent
Kinoshita et al.

(10) Patent No.: US 9,474,770 B2
(45) Date of Patent: Oct. 25, 2016

(54) PROPHYLACTIC AGENT AND/OR THERAPEUTIC AGENT FOR SEPSIS

(75) Inventors: Kosaku Kinoshita, Tokyo (JP); Katsuhisa Tanjoh, Tokyo (JP); Akihiro Noda, Tokyo (JP); Atsushi Sakurai, Tokyo (JP); Tohru Tanaka, Tokyo (JP); Kiwamu Takahashi, Tokyo (JP); Motowo Nakajima, Tokyo (JP); Fuminori Abe, Tokyo (JP)

(73) Assignees: SBI Pharmaceuticals Co., Ltd., Tokyo (JP); Nihon University, Tokyo (JP)

( * ) Notice: Subject to any disclaimer, the term of this patent is extended or adjusted under 35 U.S.C. 154(b) by 9 days.

(21) Appl. No.: 14/237,407

(22) PCT Filed: Aug. 10, 2012

(86) PCT No.: PCT/JP2012/005125
§ 371 (c)(1),
(2), (4) Date: Feb. 6, 2014

(87) PCT Pub. No.: WO2013/024589
PCT Pub. Date: Feb. 21, 2013

(65) Prior Publication Data
US 2014/0186464 A1 Jul. 3, 2014

(30) Foreign Application Priority Data
Aug. 12, 2011 (JP) .................................. 2011-177203

(51) Int. Cl.
*A61K 33/26* (2006.01)
*A61K 31/197* (2006.01)
(Continued)

(52) U.S. Cl.
CPC .............. *A61K 33/26* (2013.01); *A61K 31/197* (2013.01); *A61K 31/28* (2013.01); *A61K 31/295* (2013.01); *A61K 45/06* (2013.01)

(58) Field of Classification Search
None
See application file for complete search history.

(56) References Cited

U.S. PATENT DOCUMENTS

| 2003/0158258 A1 | 8/2003 | Marti et al. |
| 2008/0026075 A1 | 1/2008 | Kondo et al. |
| 2011/0196033 A1 * | 8/2011 | Tanaka ..................... A23L 1/30 |
| | | 514/502 |

FOREIGN PATENT DOCUMENTS

| JP | 2731032 B2 | 12/1997 |
| JP | 2002-512205 A | 4/2002 |

(Continued)

OTHER PUBLICATIONS

"Sepsis Facts" accessed online on Jun. 27, 2015 at http://www.world-sepsis-day.org.*

(Continued)

*Primary Examiner* — Johann R Richter
*Assistant Examiner* — Casey Hagopian
(74) *Attorney, Agent, or Firm* — Foley & Lardner LLP

(57) ABSTRACT

The present invention provides a sepsis therapeutic drug useful for prophylaxis and treatment of sepsis. A prophylactic agent and/or a therapeutic agent for sepsis containing 5-aminolevulinic acid (5-ALA) or a derivative thereof or a pharmacologically acceptable salt of 5-ALA or the derivative as an active ingredient is prepared. The prophylactic agent and/or the therapeutic agent preferably contains a metal-containing compound such as ferrous sodium citrate in addition to the ALAs. Preferred examples of the ALAs include ALA; various esters of ALA such as methyl, ethyl, propyl, butyl, and pentyl esters; and hydrochlorides, phosphates, sulfates of ALA and the esters.

15 Claims, 1 Drawing Sheet

(51) Int. Cl.
A61K 31/28 (2006.01)
A61K 31/295 (2006.01)
A61K 45/06 (2006.01)

(56) References Cited

FOREIGN PATENT DOCUMENTS

| JP | 2006-124372 A | 5/2006 |
| JP | 2011-016753 A | 1/2011 |
| WO | WO 91/01727 A2 | 2/1991 |
| WO | WO 99/53962 A1 | 10/1999 |
| WO | WO 2006/025286 A1 | 3/2006 |
| WO | WO2006/035678 A1 | 4/2006 |
| WO | WO 2009/139156 A1 | 11/2009 |
| WO | WO 2010/050179 A1 | 5/2010 |
| WO | WO 2010050179 A1 * | 5/2010 |

OTHER PUBLICATIONS

Yende et al. "Diabetes and sepsis outcomes—it is not all bad news" Critical Care, 2009; 13(1):117, pp. 1-2.*

Gustot et al. "Severe Sepsis in Cirrhosis" Hepatology, vol. 50, No. 6, 2009, pp. 2022-2033.*

"ALA Study Results Presented at 39th Annual Meeting of the Japanese Association of Acute Medicine—Discovery of ALA's inhibitory effect on inflammatory cytokine production," SBI ALAPromo, Oct. 21, 2011, 2pages.

Suzuki et al., "Tissue-Specific Gene Expression of Heme Oxygenase-1 (HO-1) and Non-specific δ-Aminolevulinate Synthase (ALAS-N) in a Rat Model of Septic Multiple Organ Dysfunction Syndrome," Biochemical Pharmacology, 2000, 60:275-283.

Lomnitski et al., "Effects of Antioxidants Apocynin and the Natural Water-Soluble Antioxidant from Spinach on Cellular Damage Induced by Lipopolysaccharide in the Rat," Toxicologic Pathology, 2000, 28(4):580-587.

Mirochnitchenko et al., "Endotoxemia in Transgenic Mice Overexpressing Human Glutathione Peroxidases," Circ. Res., 2000, 87:289-295.

Ritter et al., "Treatment with N-acetylcysteine plus deferoxamine protects rats against oxidative stress and improves survival in sepsis," Crit. Care Med., 2004, 32:342-349.

Wilson, John X., "Mechanism of action of vitamin C in sepsis: Ascorbate modulates redox signaling in endothelium," Biofactors, 2009, 35(1):5-13.

Itoh et al., "Photodynamic Therapy for Acne Vulgaris With Topical 5-Aminolevulinic Acid," (Reprinted) Arch. Dermatol., Sep. 2000, 136:1093-1095.

* cited by examiner

PROPHYLACTIC AGENT AND/OR THERAPEUTIC AGENT FOR SEPSIS

CROSS-REFERENCE TO RELATED APPLICATIONS

This application is a National Stage application of PCT/JP2012/005125, filed Aug. 10, 2012, which claims priority from Japanese application JP 2011-177203, filed Aug. 12, 2011.

TECHNICAL FIELD

The present invention relates to a prophylactic agent and/or a therapeutic agent for sepsis. More specifically, the invention relates to a prophylactic agent and/or a therapeutic agent for sepsis containing 5-aminolevulinic acid (5-ALA) or a derivative thereof or a pharmacologically acceptable salt of 5-ALA or the derivative as an active ingredient.

BACKGROUND ART

Sepsis is regarded as a severe systemic inflammatory response syndrome (SIRS) caused by bacterial infection such as wounds, puerperium, and diseases. The character of the SIRS is hypercytokinemia, and the blood pressure is decreased by dilation of the blood vessels caused by inflammatory materials, i.e., cytokines, and toxins secreted by infected bacteria. A significant progress of hypotension causes a lack of blood flow in each site of the body to increase a risk of causing dysfunction of each organ. In order to avoid multiple organ failure, the heart increases the heart rate to increase the blood flow. This overload on the heart causes cardiac hypofunction, which leads to a chronic lack of blood supply to important organs to cause a septic shock state, resulting in "multiple organ failure." In spite of the establishment of treatment with antibiotics, it has been reported that the number of sepsis patients in the U.S. per year is 750,000 or more and that 210,000 of the patients die. The number of patients in Japan per year is estimated at 100,000. Against such background, development of effective prophylactic and therapeutic methods for sepsis has been highly demanded.

The main reasons of the high rate of deaths from sepsis are that the sepsis therapeutic drugs that have been developed until now are all for mere symptomatic therapy for secondary lesions caused by hypercytokinemia and there are no sepsis therapeutic drugs for hypercytokinemia itself. Management of bacteria in infectious diseases has been becoming possible by progress of antibiotics. However, even if the bacteria are killed, the cytokine-inducing activity is maintained and is even higher than that of live bacteria in some cases. Blood purifying therapy utilizing hemodialysis therapy (adsorption of cytokines in blood) has been devised as a therapeutic method for hypercytokinemia, but its effect is not constant, and invasiveness to the body is also high. Many therapeutic methods, including the methods described above, have so far been tried for hypercytokinemia in sepsis, but no drug or therapeutic method was scientifically effective in many patients. The rate of deaths from sepsis tends to decrease in recent years by the start of treatment in general ward, attempt of reducing the risk of nosocomial infection by a reduction in use of pulmonary artery catheter, and administration of antibiotics in early stages. The degree of the decrease is, however, obviously small. In also treatment of sepsis, some significant treatment, not yet being discovered, other than treatment with antibiotics may be present.

Meanwhile, as one of methods for treating acne vulgaris, which is caused by bacterial infection as in sepsis, photodynamic therapy (PDT) has conventionally been known. PDT is a therapeutic method involving both photosensitizer administration and light irradiation. 5-ALA itself is not photosensitizing, but is metabolized into a photosensitizing material, protoporphyrin IX (PPIX), in vivo. Accordingly, 5-ALA is used in cancer PDT (see for example, Patent Documents 1 to 3). Clinical examples of PDT of acne vulgaris with 5-ALA have been already reported, and the therapy shows outstanding effects (see for example, Non-patent Document 1). PDT is certainly effective against bacterial infection on the skin. However, in order to kill bacteria in blood as in a case of sepsis, the blood must be directly irradiated with light. However, the absorption wavelength suitable for exciting PPIX overlaps with the absorption spectrum of hemoglobin, and an excitation light source is required to be inserted into a blood vessel via, for example, a catheter. Thus, PDT against pathogens causing sepsis has a risk of promoting further infection and exacerbating infectious disease and is therefore impractical, though it is discussed. As a result, the investigation of the PDT against pathogens causing sepsis has not progressed. In addition, PDT can be a sterilization technology, but cannot work on the above-described hypercytokinemia.

5-ALA is known as an intermediate in a tetrapyrrole biosynthetic pathway that is widely present in animals, plants, and fungi and is usually biosynthesized from succinyl CoA and glycine by 5-aminolevulinic acid synthase. Photodynamic therapy using 5-ALA (hereinafter also referred to as "ALA-PDT") has also been developed and is paid attention as a therapeutic method with low invasiveness and maintaining QOL. For example, a tumor diagnostic or therapeutic agent including 5-ALA has been reported. 5-ALA is also known to be useful as a prophylactic/ameliorating agent or a therapeutic agent for adult diseases, cancer, and male infertility (see for example, Patent Documents 4 to 6).

PRIOR ART DOCUMENTS

Patent Documents

[Patent Document 1] Japanese Patent No. 2731032
[Patent Document 2] Japanese unexamined Patent Application Publication No. 2006-124372
[Patent Document 3] Japanese unexamined Patent Application Publication (Translation of PCT Application) No. 2002-512205
[Patent Document 4] International Publication No. WO2010/050179
[Patent Document 5] Japanese unexamined Patent Application Publication No. 2011-16753
[Patent Document 6] International Publication No. WO2009/139156

Non-Patent Documents

[Non-patent Document 1] Arch Dermatol, September 2000; 136: 1093-1095

SUMMARY OF THE INVENTION

Object to be Solved by the Invention

Development of a prophylactic agent and/or a therapeutic agent effective against sepsis is highly demanded. In particular, development of a prophylactic agent and/or a therapeutic agent for sepsis that is truly effective against hypercytokinemia and shows few side effects is demanded. It is an object of the present invention to provide a prophylactic agent and/or a therapeutic agent for sepsis useful for prophylaxis and treatment of sepsis.

Means to Solve the Object

The present inventors carefully examined a large amount of data of sepsis patients, such as pathological conditions, severity, progress, prognosis, clinical examination values, and results of various therapeutic methods, and further performed comprehensive follow-up survey of clinical examples reported in the past and, as a result, concluded that the most significant factor in the pathological conditions of sepsis patients is the cytokine blood level. The inventors performed screening for compounds that inhibit proinflammatory cytokines and further continued the investigation and have found surprisingly that 5-ALA has an effect of inhibiting proinflammatory cytokines. Note that though 5-ALA is known to show bactericidal activity in PDT with light irradiation as described in "Background Art," the present invention does not need light irradiation.

5-ALA is conventionally known as a health food having various health-promoting effects, but has never been expected to have a surprising effect of inhibiting proinflammatory cytokines, which are causative substances of hypercytokinemia. It is obvious that this effect is achieved by an obviously different mechanism from those of antioxidant effect and immunostimulating reaction of 5-ALA, which have been already discovered by the present inventors. As described above, since no antibiotics can be effective against hypercytokinemia, the mechanism cannot be described as a mere antibacterial action. What mechanism is responsible for inhibition of proinflammatory cytokines by 5-ALA requires future research.

The present inventors further continued various investigations on routes of administration, combinations with drugs against secondary lesions caused by hypercytokinemia, doses, and other factors. The inventors established a therapeutic agent and a prophylactic agent for sepsis containing 5-ALA and an iron preparation as active ingredients and have accomplished the present invention.

That is, the present invention relates to:

(1) A prophylactic agent and/or a therapeutic agent for sepsis, comprising:
a compound represented by the following formula (I):

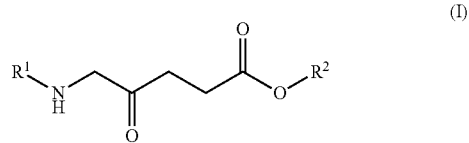

(I)

(wherein $R^1$ represents a hydrogen atom or an acyl group; and $R^2$ represents a hydrogen atom, a linear or branched alkyl group, a cycloalkyl group, an aryl group, or an aralkyl group), or a salt thereof;

(2) The prophylactic agent and/or the therapeutic agent for sepsis according to aspect (1), wherein $R^1$ and $R^2$ represent a hydrogen atom;

(3) The prophylactic agent and/or the therapeutic agent for sepsis according to aspect (1) or (2), further comprising one or more metal-containing compounds;

(4) The prophylactic agent and/or the therapeutic agent for sepsis according to aspect (3), wherein the metal-containing compound is an iron compound, a magnesium compound, a zinc compound, a nickel compound, a vanadium compound, a copper compound, a chromium compound, a molybdenum compound, or a cobalt compound;

(5) The prophylactic agent and/or the therapeutic agent for sepsis according to aspect (4), wherein the metal-containing compound is an iron compound;

(6) The prophylactic agent and/or the therapeutic agent for sepsis according to aspect (5), wherein the iron compound is one or more iron compounds selected from ferric chloride, iron sesquioxide, iron sulfate, ferrous pyrophosphate, ferrous citrate, iron sodium citrate, ferrous sodium citrate, iron ammonium citrate, ferric pyrophosphate, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron sodium dicarboxymethylglutamate, iron ammonium dicarboxymethylglutamate, ferrous fumarate, iron acetate, iron oxalate, ferrous succinate, iron and sodium succinate citrate, heme iron, iron dextran, iron triethylenetetramine, iron lactoferrin, iron transferrin, iron chlorophyllin sodium, iron ferritin, saccharated iron oxide, and sulfide glycine iron;

(7) The prophylactic agent and/or the therapeutic agent for sepsis according to aspect (6), wherein the iron compound is ferrous sodium citrate; and (8) The prophylactic agent and/or the therapeutic agent for sepsis according to any one of aspects (1) to (7), wherein the agent is used for inhibiting production of IL-6 and/or IL-8.

The present invention further relates to (9) a method for prophylaxis and/or treatment of sepsis, comprising administering to a subject a compound represented by formula (I) or a salt thereof; and (10) a method for prophylaxis and/or treatment of sepsis, comprising administering to a subject a prophylactic agent and/or a therapeutic agent for sepsis according to any one of aspects (1) to (8).

Other embodiments of aspect (9) include the method wherein $R^1$ and $R^2$ represent a hydrogen atom; the method wherein the agent contains one or more metal-containing compounds; the method wherein the metal-containing compound is an iron compound, a magnesium compound, a zinc compound, a nickel compound, a vanadium compound, a copper compound, a chromium compound, a molybdenum compound, or a cobalt compound; the method wherein the metal-containing compound is an iron compound; the method wherein the iron compound is one or more iron compounds selected from ferric chloride, iron sesquioxide, iron sulfate, ferrous pyrophosphate, ferrous citrate, iron sodium citrate, ferrous sodium citrate, iron ammonium citrate, ferric pyrophosphate, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron sodium dicarboxymethylglutamate, iron ammonium dicarboxymethylglutamate, ferrous fumarate, iron acetate, iron oxalate, ferrous succinate, iron and sodium succinate citrate, heme iron, iron dextran, iron triethylenetetramine, iron lactoferrin, iron transferrin, iron chlorophyllin sodium, iron ferritin, saccharated iron oxide, and sulfide glycine iron; and the method wherein the iron compound is ferrous sodium citrate.

The present invention further relates to (11) a compound represented by formula (I) or a salt thereof for prophylaxis and/or treatment of sepsis.

Other embodiments of aspect (11) include 5-ALA or a salt thereof for use in prophylaxis and/or treatment of sepsis; a compound represented by formula (I) or a salt thereof and one or more metal-containing compounds for use in prophylaxis and/or treatment of sepsis; the invention described above wherein the metal-containing compound is an iron compound, a magnesium compound, a zinc compound, a nickel compound, a vanadium compound, a copper compound, a chromium compound, a molybdenum compound, or a cobalt compound; the invention described above wherein the metal-containing compound is an iron compound; the invention described above wherein the iron compound is one or more iron compounds selected from ferric chloride, iron sesquioxide, iron sulfate, ferrous pyrophosphate, ferrous citrate, iron sodium citrate, ferrous sodium citrate, iron ammonium citrate, ferric pyrophosphate, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron sodium dicarboxymethylglutamate, iron ammonium dicarboxymethylglutamate, ferrous fumarate, iron acetate, iron oxalate, ferrous succinate, iron and sodium succinate citrate, heme iron, iron dextran, iron triethylenetetramine, iron lactoferrin, iron transferrin, iron chlorophyllin sodium, iron ferritin, saccharated iron oxide, and sulfide glycine iron; and the invention described above wherein the iron compound is ferrous sodium citrate.

The present invention further relates to (12) a kit for prophylaxis and/or treatment of sepsis, comprising a) a compound represented by formula (I) or a salt thereof; and b) a metal-containing compound.

The present invention further relates to (13) a method for prophylaxis and/or treatment of sepsis, comprising administering to a subject, a) a compound represented by formula (I) or a salt thereof; and b) a metal-containing compound, simultaneously or one after another.

The present invention further relates to:

(14) a combination of a prophylactic drug and/or a therapeutic drug comprising a) a prophylactic agent and/or a therapeutic agent for sepsis according to any one of aspects (1) to (8); and b) a prophylactic, therapeutic, or concomitant agent for sepsis; and

(15) a combination of a prophylactic drug and/or a therapeutic drug comprising a) a compound represented by formula (I) or a salt thereof; b) a metal-containing compound; and c) a prophylactic, therapeutic, or concomitant agent for sepsis.

The present invention further relates to (16) a use of a) a compound represented by formula (I) or a salt thereof in production of a prophylactic agent and/or a therapeutic agent for sepsis.

Other embodiments of the present invention include an IL-6 and/or IL-8 production inhibitor containing ALAs or ALAs and a metal-containing compound; a method of inhibiting production of IL-6 and/or IL-8 by administering ALAs or ALAs and a metal-containing compound to a subject; ALAs or ALAs and a metal-containing compound for use in inhibiting production of IL-6 and/or IL-8; a kit including ALAs and a metal-containing compound for inhibiting production of IL-6 and/or IL-8; a method of inhibiting production of IL-6 and/or IL-8 by simultaneously or sequentially administering ALAs and a metal-containing compound to a subject; a combination of a prophylactic drug and/or a therapeutic drug comprising the IL-6 and/or IL-8 production inhibitor and a prophylactic, therapeutic, or concomitant agent for sepsis; a combination of a prophylactic drug and/or a therapeutic drug comprising ALAs, a metal-containing compound, and a prophylactic, therapeutic, or concomitant agent for sepsis; and a use of ALAs in production of an IL-6 and/or IL-8 production inhibitor.

Effect of the Invention

The prophylactic agent and/or the therapeutic agent for sepsis containing ALAs of the present invention as active ingredients has excellent therapeutic effect and prophylactic effect against sepsis. A combination use of the agent with an existing sepsis therapeutic drug enhances the effect on the treatment of hypercytokinemia, which has been impossible until now, or has an effect of decreasing the dose of an existing sepsis therapeutic drug showing strong side effects. The mechanism of the prophylactic agent and/or the therapeutic drug for sepsis of the present invention is believed to be completely different from those of existing sepsis therapeutic drugs.

MODE OF CARRYING OUT THE INVENTION

Figure 1:
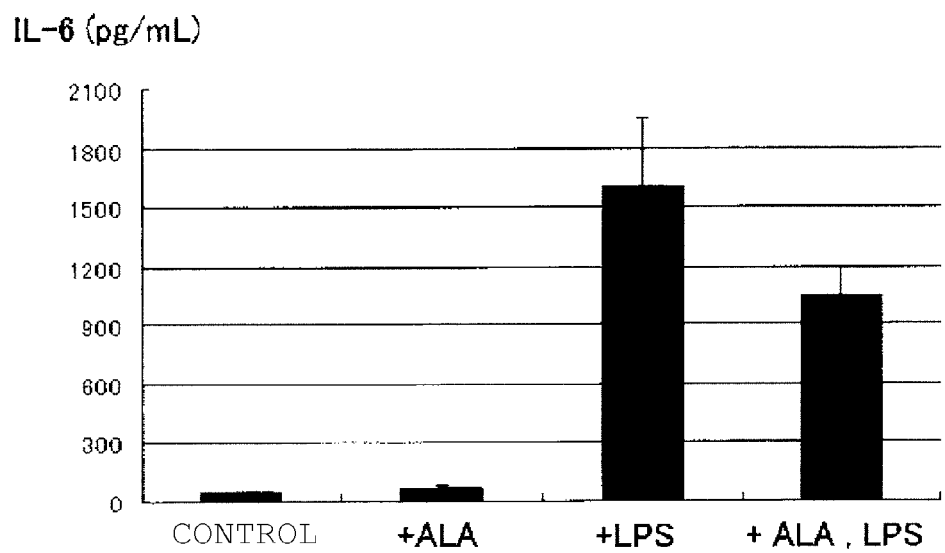
FIG. 1 is a graph showing the results of ELISA measuring IL-6 in the supernatant using a sepsis model prepared by mixed culture of human pulmonary artery endothelial cells with lipopolysaccharide (LPS) in the presence of ALA.

The prophylactic agent and/or the therapeutic agent for sepsis of the present invention is not particularly limited as long as it is an agent containing a compound represented by formula (I) or a salt thereof (ALAs) as an active ingredient and may further contain a metal-containing compound such as an iron compound. Furthermore, the agent is preferably capable of being used for inhibiting production of IL-6 and/or IL-8. The prophylactic agent and/or the therapeutic agent for sepsis of the present invention can also be used as a drug, a quasi-drug, a food, a feed, a feeding stuff, or a pet food. In the method for prophylaxis and/or treatment of sepsis of the present invention, the prophylactic agent and/or the therapeutic agent for sepsis of the present invention is administered to a subject such as a human, a domestic animal, a domestic fowl, or a pet. Prophylactic agents and/or therapeutic agents for sepsis that contain only ALAs and do not contain metal-containing compounds such as iron compounds as active ingredients are particularly effective for subjects who separately ingest compounds such as iron compounds or for subjects having high concentrations of compounds such as iron compounds in vivo.

The kit for prophylaxis and/or treatment of sepsis of the present invention is not particularly limited as long as it is a kit that separately includes ALAs and a metal-containing compound such as an iron compound as active ingredients. The kit is preferably capable of being used for inhibiting production of IL-6 and/or IL-8. In the method for prophylaxis and/or treatment of sepsis of the present invention using such a kit for prophylaxis and/or treatment of sepsis of the present invention, ALAs and a metal-containing compound such as an iron compound are simultaneously or sequentially administered to a subject such as a human, a domestic animal, a domestic fowl, or a pet.

The combination of a prophylactic drug and/or a therapeutic drug of the present invention is not particularly limited as long as it is a combination of a prophylactic agent and/or a therapeutic agent for sepsis of the present invention and a prophylactic, therapeutic, or concomitant agent for sepsis or a combination of ALAs, a metal-containing compound such as an iron compound, and a prophylactic, therapeutic, or concomitant agent for sepsis. Administration of such a combination of a prophylactic drug and/or a therapeutic drug can also prevent and/or treat sepsis. Each preparation (ingredient) of these combinations may be simultaneously or separately administered.

The present invention also relates to ALAs for use in prophylaxis and/or treatment of sepsis; and ALAs and a metal-containing compound such as an iron compound for use in prophylaxis and/or treatment of sepsis. The present invention also relates to a use of ALAs in production of a prophylactic agent and/or a therapeutic agent for sepsis; and a use of ALAs and a metal-containing compound such as an iron compound in production of a prophylactic agent and/or a therapeutic agent for sepsis.

Among the ALAs, 5-ALA in which $R^1$ and $R^2$ of formula (I) each represent a hydrogen atom or a salt of 5-ALA can be preferably exemplified. 5-ALA is one of amino acids and is also called δ-aminolevulinic acid. Examples of 5-ALA derivatives include compounds, other than 5-ALA, in which $R^1$ of formula (I) represents a hydrogen atom or an acyl group; and $R^2$ of formula (I) represents a hydrogen atom, a linear or branched alkyl group, a cycloalkyl group, an aryl group, or an aralkyl group.

Examples of the alkyl group in formula (I) include linear or branched alkyl groups having 1 to 8 carbon atoms such as methyl, ethyl, propyl, isopropyl, butyl, isobutyl, sec-butyl, tert-butyl, pentyl, isopentyl, neopentyl, hexyl, heptyl, and octyl groups.

Examples of the cycloalkyl group in formula (I) include saturated or optionally partially unsaturated cycloalkyl having 3 to 8 carbon atoms such as cyclopropyl, cyclobutyl, cyclopentyl, cyclohexyl, cycloheptyl, cyclooctyl, cyclododecyl, and 1-cyclohexenyl.

In the aralkyl group in formula (I), the aryl moiety is synonymous with the aryl group mentioned below, and the alkyl moiety is synonymous with the alkyl group mentioned above. Examples of the aralkyl group include aralkyl having 7 to 15 carbon atoms such as benzyl, phenethyl, phenylpropyl, phenylbutyl, benzhydryl, trityl, naphthylmethyl, and naphthylethyl.

Examples of the aryl group in formula (I) include aryl having 6 to 14 carbon atoms such as phenyl, naphthyl, anthryl, and phenanthryl.

Examples of the acyl group in formula (I) include linear or branched alkanoyl groups having 1 to 8 carbon atoms such as formyl, acetyl, propionyl, butyryl, isobutyryl, valeryl, isovaleryl, pivaloyl, hexanoyl, octanoyl, and benzylcarbonyl; and aroyl groups having 7 to carbon atoms such as benzoyl, 1-naphthoyl, and 2-naphthoyl.

Examples of the ALA derivatives used in the present invention include compounds in which the amino group of ALA is acylated and the carboxyl group is esterified. Preferred examples of such compounds include compounds in which the acyl group is formyl, acetyl, propionyl, or butyryl; compounds in which the ester group is methyl ester, ethyl ester, propyl ester, butyl ester, or pentyl ester; and compounds having combinations of formyl and methyl ester, acetyl and methyl ester, propionyl and methyl ester, butyryl and methyl ester, formyl and ethyl ester group, acetyl and ethyl ester, propionyl and ethyl ester, or butyryl and ethyl ester.

Examples of pharmacologically acceptable salts of ALA or ALA derivatives include pharmacologically acceptable acid addition salts, metal salts, ammonium salts, and organic amine addition salts. Examples of the acid addition salts include inorganic acid salts such as hydrochlorides, hydrobromides, hydroiodides, phosphates, nitrates, and sulfates; and organic acid addition salts such as formates, acetates, propionates, toluenesulfonates, succinates, oxalates, lactates, tartrates, glycolates, methanesulfonates, butyrates, valerates, citrates, fumarates, maleates, and malates. Examples of the metal salts include alkali metal salts such as lithium salts, sodium salts, and potassium salts; alkali earth metal salts such as magnesium salts and calcium salts; and metal salts such as aluminum and zinc salts. Examples of the ammonium salts include ammonium salts and alkylammonium salts such as tetramethylammonium salts. Examples of the organic amine salts include triethylamine salts, piperidine salts, morpholine salts, and toluidine salts.

The ALA or ALA derivative can be produced by any method of chemical synthesis, production by microorganisms, or production by enzyme. For example, an acyl group on the amino group and an ester group on the carboxyl group of an ALA derivative can be produced through acylation of the amino group and esterification of the carboxyl group by common chemical synthesis.

In order to prepare a salt of ALA represented by formula (I) or an ALA derivative, when the compound represented by formula (I) is provided in a salt form, the compound may be directly purified; and when the compound is provided in a free form, a salt thereof may be formed by dissolving or suspending the compound in an appropriate organic solvent and adding an acid or base thereto by a common method.

The ALAs may also exist in adduct forms with water or another solvent, and these adducts can be used in the prophylactic agent and/or the therapeutic agent for sepsis or another embodiment of the present invention.

ALAs, e.g., ALA, ALA derivatives, and salts thereof, that can be used in the prophylactic agent and/or the therapeutic agent for sepsis or another embodiment of the present invention may be used singly or in an appropriate combination of two or more thereof. The ALA, ALA derivatives, and salts thereof are preferably, for example, ALA; various esters of ALA such as methyl ester, ethyl ester, propyl ester, butyl ester, and pentyl ester; and hydrochlorides, phosphates, and sulfates of ALA and the esters. Most preferred compounds are hydrochlorides and phosphates of ALA.

The prophylactic agent and/or the therapeutic agent for sepsis of the present invention can also contain a metal-containing compound together with the ALAs. The metal-containing compound can be used within a range that does not cause excess symptoms. For example, the molar ratio of the metal-containing compound to the ALAs is 1:0.01 to 1:10, preferably 1:0.1 to 1:5, and more preferably 1:0.2 to 1:2.

Examples of the metal-containing compound include iron compounds, magnesium compounds, zinc compounds, nickel compounds, vanadium compounds, cobalt compounds, copper compounds, chromium compounds, and molybdenum compounds. Among these compounds, preferred are iron compounds, magnesium compounds, and zinc compounds, and particularly preferred are iron compounds. The metal-containing compound means a compound including the metal in the molecule and does not have any limitation as long as it does not impair the effect of the present invention. Examples of the iron compound including iron in the molecule include ferrous citrate, iron sodium citrate, iron ammonium citrate, ferric pyrophosphate, heme iron, iron dextran, iron lactate, ferrous gluconate, iron sodium diethylenetriaminepentaacetate, iron ammonium diethylenetriaminepentaacetate, iron sodium ethylenediaminetetraacetate, iron ammonium ethylenediaminepentaacetate, iron triethylenetetramine, iron sodium dicarboxymethylglutamate, ammonium iron ammonium dicarboxymethylglutamate, iron lactoferrin, iron transferrin, ferric chloride, iron sesquioxide, iron chlorophyllin sodium, iron ferritin, ferrous fumarate, ferrous pyrophosphate, saccharated iron oxide, iron acetate, iron oxalate, ferrous succinate, iron and sodium succinate citrate, iron sulfate, and sulfide glycine iron. In particular, ferrous citrate and iron sodium citrate are preferred.

Preferred examples of the magnesium compound including magnesium in the molecule include magnesium citrate, magnesium benzoate, magnesium acetate, magnesium oxide, magnesium chloride, magnesium hydroxide, magnesium carbonate, magnesium sulfate, magnesium silicate, magnesium nitrate, magnesium diammonium diethylenetriaminepentaacetate, magnesium disodium ethylenediaminetetraacetate, and magnesium protoporphyrin.

Preferred examples of the zinc compound including zinc in the molecule include zinc chloride, zinc oxide, zinc nitrate, zinc carbonate, zinc sulfate, zinc diammonium diethylenetriaminepentaacetate, zinc disodium ethylenediaminetetraacetate, zinc protoporphyrin, and zinc-containing yeast.

These metal-containing compounds may be used singly or as a mixture of two or more thereof and may be administered simultaneously with or separately from the ALAs. The dosage form and administration mode may be the same as those of the ALAs or may be different from those of the ALAs.

In the method for prophylaxis and/or treatment of sepsis using both the ALAs of the present invention and a metal-containing compound such as an iron compound, the ALAs and the metal-containing compound may be administered as a composition containing them, alternatively, each of the ALAs and the metal-containing compound may be administered simultaneously or one after another. In the case of independently administering each of the ALAs and the metal-containing compound, simultaneous administration thereof is preferred. In the case of independently administering each of the ALAs and the metal-containing compound sequentially, the ALAs and the metal-containing compound such as an iron compound are preferably administered such that an additive effect, preferably a synergistic effect, can be achieved.

The prophylactic agent and/or the therapeutic agent for sepsis of the present invention and the kit for prophylaxis and/or treatment of sepsis of the present invention can be used together with an existing prophylactic, therapeutic, or concomitant agent (agent used together with a prophylactic agent or a therapeutic agent) for sepsis, i.e., together with a prophylactic agent and/or a therapeutic agent and/or a concomitant agent. Examples of the prophylactic, therapeutic, or concomitant agent for sepsis include antibacterial agents such as penicillin, β-lactam, cephem, carbapenem, penem, lincomycin, monobactum, tetracycline, chloramphenicol, fosfomycin, new quinolone, fluoroquinolone, aminoglycoside, glycopeptide, and linezolid antibacterial agents; drugs that may be administered during treatment of sepsis, e.g., transfusion, bicarbonic acid, vasoconstrictor, thrombolytic agents, cardiotonic agents, ulcer preventive drugs, steroids, activated protein C, and blood products; and immunomodulators such as arginine, alginic acid, and omega 3. These prophylactic, therapeutic, or concomitant agents for sepsis and 5-ALA for sepsis are thought to basically differ from each other in the mechanism of the therapeutic effect. Accordingly, the significance of the concomitant use is high, and additive effect, furthermore synergistic effect in some cases, can be expected. These prophylactic, therapeutic, or concomitant agents for sepsis may be used singly or as a mixture of two or more thereof. Such a prophylactic, therapeutic, or concomitant agent for sepsis can be administered simultaneously with or separately from the prophylactic agent and/or the therapeutic agent for sepsis of the present invention. The dosage form and administration mode may be the same as or different from those of the prophylactic agent and/or the therapeutic agent for sepsis of the present invention.

The ALAs may be directly administered alone or may be administered together with other ingredients such as medicinal ingredients or nutrients if necessary. It is usually preferred to formulate ALAs into various pharmaceutical preparations. Such a pharmaceutical preparation can be produced by mixing an active ingredient with one or more pharmacologically acceptable carriers by a common method of pharmaceutics. As carriers that can be blended with ALAs, pharmaceutically acceptable inert organic or inorganic carrier materials in solid or liquid states suitable for ingestion are usually used. Specific examples of the carrier include crystalline cellulose, gelatin, lactose, starch, magnesium stearate, talc, vegetable or animal fats and oils, gum, and polyalkylene glycol.

Examples of the routes of administration of the prophylactic agent and/or the therapeutic agent for sepsis of the present invention, each ingredient of the kit for prophylaxis and/or treatment of sepsis of the present invention, and each ingredient of the combination of a prophylactic drug and/or a therapeutic drug of the present invention include oral administration including sublingual administration; and parenteral administration such as nasal administration, inhalation administration, intravenous administration including intravenous drip, dermal administration with, for example, plaster, suppository, and forced enteral nutrition using a nasogastric tube, nasoenteric tube, gastric fistula tube, or intestinal fistula tube. The existing prophylactic, therapeutic, or concomitant agent for sepsis used in the combination of the prophylactic drug and/or the therapeutic drug of the present invention is preferably administered through the administration mode that is already accepted for the drug.

The dosage forms of the prophylactic agent and/or the therapeutic agent for sepsis of the present invention, each ingredient of the kit for prophylaxis and/or treatment of sepsis of the present invention, and each ingredient of the combination of a prophylactic drug and/or a therapeutic drug of the present invention can be appropriately determined according to the routes of administration mentioned above. Examples of the formulations include injections, nasal drops, drops, tablets, capsules, fine granules, powders, liquids, solutions dissolving ingredients in syrups or the like, plasters, and suppositories. The prophylactic agent and/or the therapeutic agent for sepsis of the present invention and the each ingredient of the kit for prophylaxis and/or treatment of sepsis of the present invention may be in a form of tablet or capsule of supplement, in addition to the medicinal use. In particular, for subjects with dysphagia, such as the aged and infants, disintegrating tablet forms showing rapid disintegration in the mouth or liquid forms suitable for nasogastric tube administration are preferred. These preparations can be produced by common methods appropriately using a solvent, a dispersant, a filler, an excipient, or other additives.

In order to prepare the prophylactic agent and/or the therapeutic agent for sepsis of the present invention and the kit for prophylaxis and/or treatment of sepsis of the present invention, if necessary, pharmacologically acceptable carries, excipients, diluents, additives, disintegrants, binders, coatings, lubricating agents, glidants, lubricants, flavoring agents, sweetening agents, solubilizers, solvents, gelatinizers, and nutrients may be added; specifically, water, saline, animal fats and oils, plant oils, lactose, starch, gelatin, crystalline cellulose, gum, talc, magnesium stearate, hydroxypropyl cellulose, polyalkylene glycol, polyvinyl alcohol, and glycerin. For example, an injection may be produced by adding, for example, water, saline, a plant oil, a solubilizer, and a preservative in accordance with a common method. Tablets can be produced by mixing various additives such as lactose, starch, magnesium stearate, hydroxypropyl cellulose, polyvinyl alcohol, a surfactant, and glycerin in accordance with a common method. An inhalant can be produced by adding, for example, lactose in accordance with a common method. In the case of preparing these preparations as aqueous solutions, attention needs to be paid for the aqueous solutions not to become alkaline for preventing decomposition of compound (I). If the solution becomes alkaline, the decomposition of the active ingredient can be prevented by removing oxygen.

The prophylactic agent and/or the therapeutic agent for sepsis of the present invention and the kit for prophylaxis and/or treatment of sepsis of the present invention can be applied not only to humans but also to domestic animals, domestic fowls, and pets as veterinary medicine. The dose, frequency, and period of administration of the prophylactic agent and/or the therapeutic agent when the subject is a human vary depending on the age, weight, symptoms, and other factors of the sepsis patient. The dose of ALAs contained in a preparation can be usually 1 mg to 3000 mg, preferably 3 mg to 1000 mg, and more preferably 10 mg to 700 mg for an adult as the amount in terms of ALA hydrochloride converted from the total number of moles of the ALAs. The time of administration is not restricted and may be in the morning or in the evening. The administration is preferably once a day or several times per day when the dose is large. The number of days of ingestion varies depending on the symptoms, and the ingestion is preferably continued for 3 to 4 days after easing of the symptoms.

The present invention will be more specifically described by the following example, which, however, should not be construed to restrict the technical scope of the present invention.

Example 1

The following experiment of measuring IL-6 (FIG. 1) and IL-8 (FIG. 2) in a sepsis model by ELISA was performed using a supernatant prepared by mixed culture of human pulmonary artery endothelial cells with lipopolysaccharide (LPS) having an activity of promoting the secretion of proinflammatory cytokines. Since the lung is an organ that is most frequently damaged by sepsis, human pulmonary artery endothelial cells were used in the experiment.

Human pulmonary artery endothelial cells were divided into the following four groups (each $5 \times 10^5$ cells/well, n=3 wells) on the basis of whether or not LPS and 5-ALA were added to the culture medium:

(1) Control without stimulation (Control in each figure),
(2) Mixed culture for 3 hours after addition of 5-ALA (100 μM) (+ALA in each figure),
(3) Mixed culture for 3 hours after addition of LPS (1 μg/mL) (+LPS in each figure), and
(4) Mixed culture for 3 hours after addition of 5-ALA (100 μM) and LPS (1 μg/mL) (+ALA, LPS in each figure).

To each of the groups containing 5-ALA, ferrous sodium citrate was also added at a molar ratio of 5-ALA:ferrous sodium citrate=1:0.5.

Figure 2:
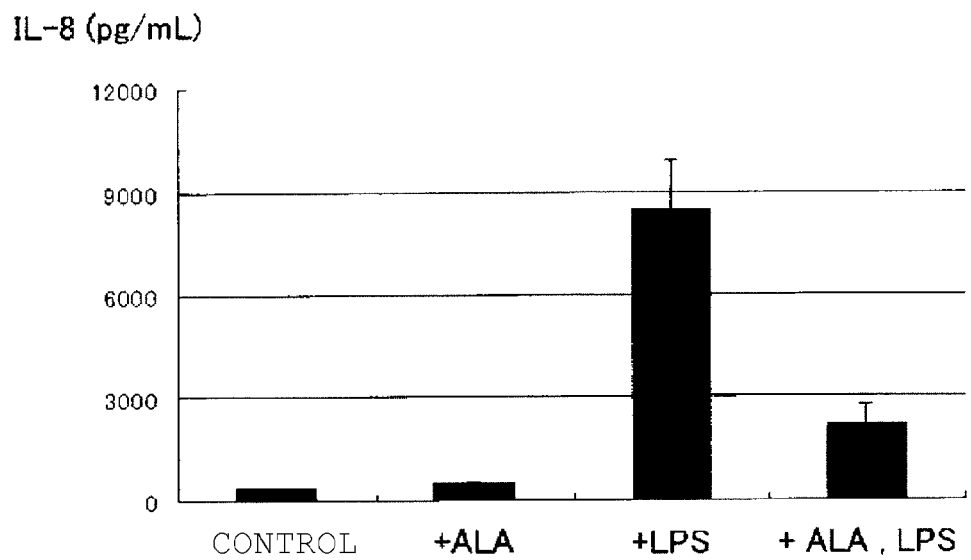
FIG. 2 is a graph showing the results of ELISA measuring IL-8 in the supernatant using a sepsis model prepared by mixed culture of human pulmonary artery endothelial cells with LPS in the presence of ALA.

As a result, in a sepsis model prepared by stimulating the human pulmonary artery endothelial cells with LPS to promote the secretion of proinflammatory cytokines, inhibition of production of proinflammatory cytokines, IL-6 and IL-8, was observed in mixed culture after addition of 5-ALA and ferrous sodium citrate (n=3, FIGS. 1 and 2: +ALA, LPS).

INDUSTRIAL APPLICABILITY

The prophylactic agent and/or the therapeutic agent for sepsis of the present invention can be advantageously used in the field of medicine.

The invention claimed is:
1. A method for treating sepsis comprising:
administering to a subject having sepsis a compound represented by the following formula (I):

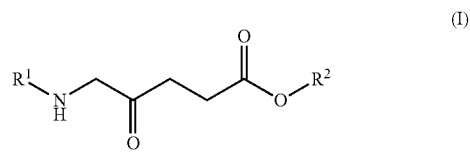

(wherein $R^1$ represents a hydrogen atom or an acyl group; and $R^2$ represents a hydrogen atom, a linear or branched alkyl group, a cycloalkyl group, an aryl group, or an aralkyl group), or a salt thereof.

2. The method for treating sepsis according to claim 1, wherein $R^1$ and $R^2$ represent a hydrogen atom.

3. The method for treating sepsis according to claim 1, further comprising administering to the subject one or more metal-containing compounds.

4. The method for treating sepsis according to claim 3, wherein the metal-containing compound is an iron compound, a magnesium compound, a zinc compound, a nickel compound, a vanadium compound, a copper compound, a chromium compound, a molybdenum compound, or a cobalt compound.

5. The method for treating sepsis according to claim 4, wherein the metal-containing compound is an iron compound.

6. The method for treating sepsis according to claim 5, wherein the iron compound is one or more iron compounds selected from ferric chloride, iron sesquioxide, iron sulfate, ferrous pyrophosphate, ferrous citrate, iron sodium citrate, ferrous sodium citrate, iron ammonium citrate, ferric pyrophosphate, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron sodium dicarboxymethylglutamate, iron ammonium dicarboxymethylglutamate, ferrous fumarate, iron acetate, iron oxalate, ferrous succinate, iron and sodium succinate citrate, heme iron, iron dextran, iron triethylenetetramine, iron lactoferrin, iron transferrin, iron chlorophyllin sodium, iron ferritin, saccharated iron oxide, and sulfide glycine iron.

7. The method for treating sepsis according to claim 6, wherein the iron compound is ferrous sodium citrate.

8. The method for treating sepsis according to claim 1, wherein sepsis is treated by inhibiting production of IL-6 and/or IL-8.

9. The method for treating sepsis according to claim 2, further comprising administering to a subject having sepsis one or more metal-containing compounds.

10. The method for treating sepsis according to claim 2, wherein sepsis is treated by inhibiting production of IL-6 and/or IL-8.

11. The method for treating sepsis according to claim 3, wherein sepsis is treated by inhibiting production of IL-6 and/or IL-8.

12. The method for treating sepsis according to claim 4, wherein sepsis is treated by inhibiting production of IL-6 and/or IL-8.

13. The method for treating sepsis according to claim 5, wherein sepsis is treated by inhibiting production of IL-6 and/or IL-8.

14. The method for treating sepsis according to claim 6, wherein sepsis is treated by inhibiting production of IL-6 and/or IL-8.

15. The method for treating sepsis according to claim 7, wherein sepsis is treated by inhibiting production of IL-6 and/or IL-8.

* * * * *